(12) United States Patent
Combes et al.

(10) Patent No.: US 8,395,086 B2
(45) Date of Patent: Mar. 12, 2013

(54) HEATER DEVICE

(75) Inventors: David J Combes, Malvern (GB); Timothy I Cox, Malvern (GB); Ian C Sage, Malvern (GB)

(73) Assignee: Qinetiq Limited, London (GB)

( * ) Notice: Subject to any disclaimer, the term of this patent is extended or adjusted under 35 U.S.C. 154(b) by 1072 days.

(21) Appl. No.: 12/271,233

(22) Filed: Nov. 14, 2008

(65) Prior Publication Data

US 2009/0211336 A1     Aug. 27, 2009

Related U.S. Application Data

(60) Provisional application No. 61/064,238, filed on Feb. 22, 2008.

(51) Int. Cl.
| | |
|---|---|
| H05B 3/10 | (2006.01) |
| H05B 3/22 | (2006.01) |
| G01N 1/22 | (2006.01) |
| G01N 33/00 | (2006.01) |
| B01D 53/04 | (2006.01) |

(52) U.S. Cl. ......... 219/201; 219/552; 422/68.1; 422/88; 422/98; 392/485; 73/25.05

(58) Field of Classification Search .................. None
See application file for complete search history.

(56) References Cited

U.S. PATENT DOCUMENTS

| | | | |
|---|---|---|---|
| 6,084,217 A | 7/2000 | Bulgajewski | |
| 6,097,011 A | 8/2000 | Gadkaree et al. | |
| 6,171,378 B1 * | 1/2001 | Manginell et al. | 96/143 |
| 6,527,835 B1 | 3/2003 | Manginell et al. | |
| 6,914,220 B2 * | 7/2005 | Tian et al. | 219/408 |
| 7,118,712 B1 | 10/2006 | Manginell et al. | |
| 7,306,649 B2 * | 12/2007 | Boyle et al. | 95/82 |
| 8,137,979 B2 * | 3/2012 | Combes et al. | 436/106 |
| 2004/0056016 A1 | 3/2004 | Tian et al. | |
| 2005/0226778 A1 * | 10/2005 | Houser et al. | 422/99 |
| 2007/0084347 A1 * | 4/2007 | Boyle et al. | 96/101 |
| 2008/0121103 A1 * | 5/2008 | Boyle et al. | 95/87 |
| 2010/0083736 A1 * | 4/2010 | Markowitz et al. | 73/23.41 |
| 2010/0120167 A1 * | 5/2010 | McGill et al. | 436/178 |
| 2010/0130796 A1 * | 5/2010 | Combes et al. | 568/935 |
| 2010/0144049 A1 * | 6/2010 | Combes et al. | 436/106 |

FOREIGN PATENT DOCUMENTS

| | | |
|---|---|---|
| WO | WO 2005/048350 | 5/2005 |
| WO | WO 2007/041551 | 4/2007 |

OTHER PUBLICATIONS

International Search Report for PCT/GB2008/002161, mailed Sep. 23, 2008.
UK Search Report for GB Application No. 0714276.3, dated Mar. 17, 2008.
Voicolescu, I. et al., "Micropreconcentrator for Enhanced Trace Detection of Explosives and Chemical Agents", IEEE Sensors Journal, vol. 6, No. 5, (Oct. 2006), pp. 1094-1103.
Mckeown, N.B. et al., "Polymers of Intrinsic Microporosity (PIMs): Bridging the Void Between Microporous and Polymeric Materials", Chemistry, vol. 11, No. 9, (Apr. 22, 2005), pp. 2610-2620.
Budd, Peter M. et al., "Gas Separation Membranes from Polymers of Intrinsic Microporosity", Journal of Membrane Science, vol. 251, (2005), pp. 263-269.
Sage, Ian et al, "Surface Modified Silicon Structures as Pre-Concentrators for Trace Chemical Detection", Gordon Research Conference, (Sep. 16-21, 2007), 22 pages.

* cited by examiner

*Primary Examiner* — Joseph M Pelham
(74) *Attorney, Agent, or Firm* — Nixon & Vanderhye P.C.

(57) ABSTRACT

Isopotential heaters used in the preconcentration stage of sample detection systems are described. The heaters have at least two electrically conducting paths of which the resistances of the electrically conducting baths are substantially equal such that in use uniform heat distribution is achieved.

31 Claims, 4 Drawing Sheets

HEATER DEVICE

This application claims priority to US Provisional Application No. 61/064,238, filed Feb. 22, 2008. The entire contents of US Provisional Application No. 61/064,238 and PCT/GB2008/002161 are hereby incorporated by reference.

This invention relates to the field of improved micro machined (MEMs scale) heaters, which are particularly suitable for use in MEMs scale preconcentrators. Preferably the heater possess a trapping medium, in particular a polymer of intrinsic microporosity (PIMs). There is further provided devices comprising the preconcentrator, and methods of preparation and use. There is particular benefit directed to the use of a MEMs scale heater coated with the PIMs for use in hand-held or field portable chemical detection devices.

A preconcentrator unit is a concentration stage of a sample detection system that is able to trap reversibly a target analyte. Typically, the analyte is present at a trace level in a large volume of carrier fluid and the preconcentrator unit increases the concentration of the analyte prior to passing it through a detector. As a result, the threshold concentration for detection of a target analyte in the sampled (carrier) fluid is reduced. Typically, the preconcentrator is placed in the path of an inlet gas which contains the analyte (the adsorption, trapping or pre-concentration phase). After a predetermined time or volume flow, the preconcentrator is switched to desorb the analyte into a detector that is capable of detecting the analyte in question (the desorption phase).

The use of preconcentrators is prolific in the field of trace detection and analysis in gaseous phases. The efficiency of a preconcentrator is determined by several factors, including the amount of adsorption and subsequent desorption of the analyte and the specificity of the preconcentrator towards the target analyte.

Preconcentrators generally comprise a trapping medium and a heating element, the heating element being configured so as to desorb the analyte from the trapping medium when required. Preconcentrators can comprise packed columns wherein the column itself is heated to effect desorption, or a membrane or film supported on a conductive-film heating element. The trapping medium may be formed from a variety of compounds such as porous sol gels, silica, silicones, metal fibres etc.

The trapping medium in a preconcentrator ideally presents sufficient strength of interaction with the target analyte to bind it efficiently under sampling conditions, but not so strongly as to prevent its rapid and substantially complete release at an accessible elevated temperature. The trapping medium desirably also provides sufficient trapping capacity for the analyte, so that it does not readily become saturated with the target material under ordinary conditions of use. In general, the trapping medium used will depend on the physical and chemical properties of the target analyte, and especially on the saturated vapour pressure of the analyte under ambient conditions and under the operating temperature conditions of the preconcentrator during the trapping phase of operation.

During the desorption phase, the trapping medium is heated to release trapped material, preferably rapidly so as to ensure that the highest possible concentration of trapped analyte passes into the detector. The trapping medium should preferably show very high thermal stability up to the maximum temperature used for desorption, and any degradation which does occur should not release vapours which interfere with the detection of the target materials by the detector. Preferably, the trapping medium/adsorbent releases substantially no interfering vapours during the desorption phase.

Sandia National Laboratories, U.S. Pat. No. 5,854,431, has developed SnifferStar® which is a micro chemical analysis system for deployment on Unmanned Aerial Vehicles (UAVs). The SnifferSTAR® consists of a microfabricated preconcentrator with a thin silicon nitride membrane supporting a patterned, metal film heating element. The Sandia device possesses a heater having a micromachined surface a few microns thick. The relatively small thickness provides a fast heat response. However, it has the inherent disadvantage of also possessing a small trapping-medium surface area, which in turn reduces the overall efficiency of the preconcentrator.

Another example of a preconcentrator, for use with explosives, has been designed by the US Naval Research Laboratory (NRL) (IEEE sensors journal, vol. 6, no. 5, October 2006). The system possesses a trapping membrane comprising a hyperbranched polycarbosilane additionally functionalised with hexafluoroispropanol (HFIP) pendant groups (also known as an HCSA2 polymer). The preconcentrator is similar to the Sandia design, with a 6 µm thick silicon element with a through flow structure. However, due to the small thickness, 6 µm, the preconcentrator again possesses a small trapping-medium surface area and hence reduced efficiency.

Prior art devices with thicker heating elements and hence, a larger surface area, tend not to be well optimised for constant temperature distribution, which is desirable for reproducible and rapid desorption. Alternatively, where heaters are optimised for rapid heating, such as the two above mentioned prior art examples, they possess a low trapping-medium surface area due to the reduced thickness and low surface area of the heating elements. One way of increasing the trapping surface area is to add a further trapping layer, but this can in turn be susceptible to decomposition after rapid heating and cooling cycles.

According to a first aspect of the invention there is provided an isopotential heater suitable for use in a preconcentrator, wherein said heater comprises at least two electrically conducting paths, wherein the electrical resistances of the at least two electrically conducting paths are substantially equal, such that in use, a uniform heat distribution is achieved. Preferably there is a plurality of electrically conducting paths each with substantially the same resistance value.

To address the problems of improving the ability of a heater to provide uniform heating profiles, there is provided according to a second aspect of the invention a micro machined heater suitable for use in a preconcentrator wherein said heater has an isopotential configuration, such that the electrical resistance of all paths through said configuration are substantially equal, such that in use a uniform heat distribution is achieved. The paths are preferably provided by a plurality of conductive bars.

The isopotential configuration may be provided by a heater comprising a plurality of conductive bars, wherein each of said conductive bars has substantially the same electrical resistance. Therefore for different length conductive bars the width (i.e. cross sectional area) of each bar may be altered to provide conductive bars with the same resistance. This may be achieved by ensuring each bar is a different width to provide equal resistance in each conductive bar. The width of each conductive bar may be uniform along its length, such that different conductive bars have different lengths and widths, or alternatively, the conductive bars may have a cross sectional area which is modulated along its length, i.e. varying the width along its length. Optionally, said conductive bars comprise adjoining crossbars, preferably thermally and electrically conductive crossbars, to increase further the surface area of the heater.

In an idealised system where electrically conducting crossbars are electrically connected to the conductive bars at isopotential points then no current will flow along said crossbar, as there is no difference in potential. Clearly, variations in tolerance may lead to slight current flow in crossbars. Conveniently, the conductive bars and crossbars are made from the same electrically and thermally conductive material.

In one preferred embodiment, the isopotential configuration is provided by a substantially circular heater comprising arcs each of which have substantially the same electrical resistance. In one arrangement the width of the arc may be uniform along its length, alternatively, the arcs may have a cross sectional area which is modulated along its length, i.e. varying the width along its length, such as to provide modulated arc widths which are proportional to the arc's length; optionally said arcs comprise adjoining struts in the form of conductive crossbars to increase further the surface area of the heater. Preferably, when the heater is circular the conductive bars are provided in the shape of an arc and any conductive crossbars are advantageously also provided in the shape of an arc. Preferably, the conductive crossbars are formed from the same material as the conductive bars, so as to permit both electrical and thermal conduction. Preferably the conductive crossbars, are modulated along their length so as to provide isopotential sections, i.e. the conductive crossbars possess substantially equal resistances between each modulated arc intersection.

In the preferred circular arrangement discussed above, the conductive crossbars in the form of arcs, span and intersect with a number of adjacent conductive bars (struts), giving rise to an open lattice heater. Preferably, the point of intersection between said conductive bars and conductive crossbars is selected at a point which corresponds to a point of electrical isopotential on said conductive bar.

Put another way, the points of intersection between the conductive bars and the conductive crossbars are selected so as to form regions of conductive bar possessing substantially the same electrical resistance. It is preferable, therefore, that the spacing between crossbars is selected to provide a conductive bar where the electrical resistance is substantially the same between each point of intersection with the conductive crossbar. If the points of intersection were not at points of isopotential it may cause electrically conducting paths which do not have substantially equal resistance, and hence may give rise to hotspots and non-uniform heating.

In the arrangement where the conductive bars and crossbars have uniform width along their length (i.e. not modulated) then the spacing between each conductive crossbar may simply be a uniform distance. Whereas in the case of conductive bars and crossbars which are modulated along their length, the spacings between respective sets of crossbars may not be regular, but must give rise to points of intersection which give rise to all electrically conducting paths having substantially the same resistance. The electrically conducting paths are the conducting pathways between the terminal contact areas.

The conductive crossbars may be heated substantially by thermal conduction from the conductive bars and some minor degree of ohmic resistance heating. The thermal characteristic response time of said conductive crossbars is preferably considerably shorter than the required heat-up time of the heater. Preferably such thermal response time is less that 500 ms, more preferably less than 20 ms, still more preferably less than 5 ms.

The temperature profile in the steady state is determined by the balance between heat loss and heat generation. The heat loss due to convection cooling for each conductive bar is a function of surface area. The surface area of each conductive bar is dominated by the depth of the conductive bar, rather than the width, in a preferred geometry approximately 5:1 depth:width. The thermal resistance is equalised when the electrical resistance is equalised. The structure therefore has a substantially uniform heat distribution in the steady state.

In a more preferred arrangement the preconcentrator heater is substantially circular and the conductive bars and conductive crossbars are both formed in arc shaped segments, wherein the conductive crossbars intersect at isopotential points on the conductive bars.

The intersection of conductive bars and conductive crossbars may define a plurality of channels or through holes, to provide a through flow heater. The number of conductive bars and conductive crossbars may be selected to alter the mechanical robustness, surface area and/or trapping efficiency of the resulting preconcentrator. The shapes of the holes or channels are defined by the shape of the conductive bars and cross bars.

The cross sectional area of the conductive bars may be adjusted in proportion to their length, such that each conductive bar has substantially equal electrical resistance.

The heater may be substantially circular and comprise individual conductive bars originating from at least two common central contact areas located at each end of the heater device. In a preferred arrangement, the isopotential heater comprises a plurality of conductive bars which are electrically connected to, and extend from, a first contact area to a second contact area, to form a heater which has an open lattice configuration.

The first and second contact areas provide the electrical connection for each of the conductive bars. In use, an electrical potential difference may be applied to the first and second contact areas such that ohmic resistive heating occurs in the heater structure.

Preferably, the cross sectional area of each conductive bar and conductive crossbar is varied along its length such that all conductive bars and crossbars have substantially the same electrical resistance when measured with respect to the two contact areas. The isopotential configuration thus-obtained facilitates achieving the optimal distribution of heat generation and heat loss across the entire surface of the heater.

The electrical resistance of the contact area on the heater, i.e. the point from which the conductive bars originate, may also be configured to improve the distribution of heat in the structure. Such improvement may, for example, comprise the introduction of a potential barrier at the contact area, such as the use of a Schottky barrier or other known forms of potential barrier which serve to increase the electrical power dissipation in the region of the contact area. The additional electrical power dissipation may compensate for heat lost at the support points of the heater or through electrical connections to the heater and thereby improve the uniformity of temperature distribution during operation of the preconcentrator.

It is preferable that the heater shape substantially corresponds with the underlying aperture in the carrier on which the heater structure is mounted. It is generally more straightforward to achieve a circular aperture. However it will be clear that other shapes, such as, for example, oval lattices, square or rectangular lattices or indeed any polygon shape may be employed.

In an alternative arrangement the heater may be formed from a solid piece of electrically conductive material with an array of perforations. The pitch and size of perforations in the conductive material determines the number of through holes, the remaining conducting material defining the heater structure, (i.e. the material which is available to conduct an electrical current). The distribution of the perforations across the conductive material may be adjusted to achieve a uniform temperature distribution by varying their pitch in proportion to their distance from the shortest path through the structure, such that longer paths through the structure are of the same electrical resistance as shorter paths.

Preferably the heater is fabricated from a material with high thermal conductivity, for example a material having a thermal conductivity at 100° C. of at least 70 $Wm^{-1}K^{-1}$, more preferably 90 $Wm^{-1}K^{-1}$, still more preferably 100 $Wm^{-1}K^{-1}$.

In a preferred arrangement the heater is micro-machined from a thermally and electrically conductive substrate material, preferably the heater is manufactured by deep ion etching. The heater may be made from any resistive material, preferably the heater is made from a metalloid, such as, for example, silicon, germanium, or a metal or an alloy thereof such as, for example, nickel, chromium, iron, copper, silver, platinum, palladium.

To improve the conductivity of a heater when constructed from a metalloid, such as, for example, silicon or germanium, it may be doped with impurities, such as, for example, phosphorous, arsenic and boron. Conveniently, when the heater is prepared from silicon it may additionally be partly anodised in a solution comprising hydrofluoric acid, to increase further the surface area of the heater by forming a porous silicon layer on said surface.

In the case that a doped metalloid is used as the base material of the heater, it is preferably doped at such a level that the temperature coefficient of resistance is large and positive over the temperature interval encompassed by the sample and desorption phases of operation. Such large positive temperature coefficient of resistance provides a measure of intrinsic power regulation to the conductive bars and contributes to maintaining a uniform temperature distribution in the heater. Such large positive temperature coefficient may for example be obtained by choice of silicon with a doping level in the region of $10^{14}$ to $10^{17}$ per cubic centimeter. In other words, if a particular path gets too hot, then the heat input ($V^2/R$) falls and the heating rate falls so that other cooler paths may catch up.

The flow-through heater is preferably formed from an electrically conductive material possessing a high thermal conductivity and is further mounted on a non-conducting carrier (i.e. support) which has a low thermal conductivity. To permit through flow from the heater the carrier has an aperture located under the heater structure. Preferably, the thermal conductivity of the carrier at 100° C. is less than 20 $Wm^{-1}K^{-1}$, more preferably less than 5 $Wm^{-1}K^{-1}$, still preferably less than 1 $Wm^{-1}K^{-1}$. The heater structure may be preferably formed from doped silicon and the carrier formed from glass. Thermal conductivity in glass is approximately $\frac{1}{100}$ of that in silicon, and this may be used to thermally isolate the heater structure from the other components of the preconcentrator. The thermal isolation of the heater may be modified by adjusting the thickness of the carrier and the total surface area of heater in contact. The contact area between the heater and carrier may be limited to that only necessary to support bonding areas. Additional contact areas may be used to ensure mechanical robustness, such as, for example, at the periphery of the heater structure.

The heater according to the invention may be manufactured to any dimension, suitable for installation within a preconcentrator for use in portable chemical detector.

According to a third aspect of the invention there is provided preconcentrator device comprising a sampling platform for reversibly adsorbing an organic analyte, comprising a heater according to the invention as defined hereinbefore, and optionally a trapping medium applied to the surface of said heater, preferably the trapping medium is a polymer of intrinsic microporosity.

The heater is preferably formed into an open lattice configuration to allow a flow of inlet gas through said lattice. The lattice configuration of the heater also allows for the conductive bars, conductive crossbars (struts and arcs for circular heaters) and cavities formed therein to be coated with trapping media, such as PIMs, thereby increasing further the surface area of the heater and hence the surface area of the trapping medium.

The heater according to the invention allows for a large surface area of the PIMs trapping medium material to be achieved and yet still permit rapid and uniform heating of the heater and thus the PIMs to allow desorption of the analyte. Preferably, for use in a portable device, the heater has a diameter of less than 25 mm, more preferably a diameter of less than 7 mm, yet more preferably in the range of 2 mm to 6 mm.

When the heater is in the form of an open lattice, its thickness will also determine the available surface area and physical strength. Additionally, the thickness will determine the electrical resistance, which will in turn determine the time of the heating profile. The heater according to the second aspect of the invention preferably has a thickness of less than 1000 microns, more preferably less than 600 microns, yet more preferably in the range of 100 to 500 microns. This provides a heater capable of rapid heating in the range of 150° C. to 225° C., preferably to at least 200° C., preferably in less than one second when supplied with an electrical power input preferably of around 1-2 Watt per square centimeter of available surface area.

The heater preferably has an open lattice structure with a total surface area of at least 20 $mm^2$, more preferably at least 100 $mm^2$.

Preferably the through holes in the preferred through flow heater have a width across their smallest dimension of from 10 to 250 microns, more preferably 20 to 150 microns, still more preferably 25 to 100 microns. The radius of the through holes is preferably less than the diffusion distance of the analyte molecules over their transit time through the heater structure, and is chosen to be sufficiently large to allow coating of the holes with the trapping material, such as PIMs materials. The holes may be substantially circular in nature, so the radius would be an effective radius.

Many of the thin film heaters used with preconcentrators in the prior art do not usually possess an open lattice or through flow structure. Typically, they use a solid element to support a substantially solid layer of membrane trapping media. Therefore, the preconcentrator structures of the prior art are located such that the air flow is parallel to the surface of the membrane.

The preferred open lattice heater of the present invention, may be coated with any trapping medium, or with a PIMs material coating, and may be mounted in any orientation within the path of the inlet gas flow. Preferably the surface of the heater is positioned substantially perpendicular to the direction of said gas flow. This allows for more of the analyte to pass across the surface of the heater and trapping medium such as, for example, PIMs. A yet further advantage is that an open lattice will permit a coating of the PIMs material on the front surface and all exposed surfaces of the conductive substrate heater material including the cavities within the lattice and, optionally, the rear surface of the heater where unsupported. The size of the holes in the lattice will affect the through flow of air. To improve further the flow through the lattice, it may be desirable to increase the size of the holes in the lattice, such as, for example, by using fewer conductive bars and conductive crossbars (struts and arcs) in the isopotential structure.

Conveniently, there is provided a preconcentrator device comprising a sampling platform for reversibly adsorbing an organic analyte, said sampling platform comprising an element which has deposited thereon at least one polymer of intrinsic microporosity and a heating means to heat said polymer of intrinsic microporosity.

The heating means may be any commonly used heater or heating means which is capable of heating the polymer of intrinsic microporosity (PIMs) coating. The heat may be supplied to the PIMs in the form of conduction (optionally via the element), radiation or convection type means. In a preferred arrangement the element itself is the heater, in other words, the heater and element form an integral component. The heater might be, for example, an ohmic heating element. This preferred arrangement provides a preconcentrator device comprising a sampling platform for reversibly adsorbing an organic analyte, wherein said sampling platform comprises a heater which has deposited thereon a trapping medium comprising at least one polymer of intrinsic microporosity. Preferably the heater is a heater according to the invention.

It is highly desirable to use a trapping medium, such as PIMS, which possesses a high affinity and selectivity for particular target analytes, and is also thermally stable at the temperature of desorption, so as to optimise preconcentration parameters.

PIMs are particularly suitable trapping media in this regard, for the following reasons. Many adsorbents provide either an effective increase in the available surface area of the preconcentrator or alternatively a liquid-like film to increase the affinity of the preconcentrator to the analyte vapour. Such materials offer limited opportunities to vary the binding strength between an analyte and the trapping medium by design. A particular disadvantage with granular and insoluble adsorbents is the difficulty in achieving rapid analyte desorption through fast and uniform heating.

Thus, a problem is not necessarily in finding a trapping medium which is able to collect and trap 100% of the analyte which is present. One problem is instead finding a trapping medium which can reversibly adsorb the target analyte; such that it may be easily removed/desorbed from the trapping medium for detection at a later predetermined stage and whilst retaining thermal integrity.

The present inventors have found that polymers of intrinsic microporosity provide a reversible trapping medium, which is advantageous for use in a preconcentrator. Polymers of intrinsic microporosity, hereinafter also referred to as PIMs, have been found to provide a highly efficient trapping medium for use in preconcentrators, said polymers being particularly useful for high throughput (i.e. high volume) gas flow preconcentrator systems. Further advantage is found in that PIMs coatings posses a high partition coefficient with organic compounds, particularly small aromatic compounds, which means that these compounds can be selectively adsorbed. The stability of the polymer at high temperatures, such as, for example, in the region of 200° C., allows for the ready desorption of the target analyte, without comprise to the structural integrity to the PIMs. Inorganic materials used as heterogeneous catalysts and adsorbents contain macro- meso- and microporous structures due to the high surface area provided by their lattice networks. Polymers of intrinsic microporosity were first synthesised by McKeown et al CHEM. COMMUN., 2002, pages 2780-2781 and ibid pages 2782-2783. McKeown reported a new microporous (nano sized pores) material, made by the linking of rigid organic molecules. The per se PIMs compounds are also reported in patent applications WO05113121, US2004198587 and EP1648954. McKeown et al report the use of PIMs as barrier/diffusion membranes, whereby a concentration gradient of components may be set up on either side of a membrane layer.

WO05113121 is directed to an improved composite diffusion membrane formed from a PIMs material supported on a high porosity supporting layer with a mean pore size less than 25 nm.

US2004198587 is directed to porphyrinic polymers per se and their methods of synthesis. EP1648954 is directed to PIMs polymers, and expressly disclaims porphyrinic polymers. The uses in both applications are directed towards diffusion membranes.

There are many membrane materials which are used in chemical separations and purification, often with excellent pervaporation capabilities. However, although many of these membranes possess excellent permeation properties, they are generally not required or optimised to trap trace chemicals. They may also be poor at releasing the trapped analyte, due to strong chemical and/or physical interactions between the membrane and analyte.

It is also well-known that the affinity of a membrane for an analyte may be further increased by the incorporation of functional groups. However, this commonly leads to low thermal stability due to decomposition of the functional groups encompassed in the membrane material. As mentioned above, high thermal stability is a desirable feature for a preconcentrator trapping medium, due to the constantly repeated heating and cooling cycles during operation. The PIMs polymers have unexpectedly been found to exhibit high thermal stability, up to 200° C., which is a useful range for preconcentrator devices.

Polymers of intrinsic microporosity comprise a rigid and contorted polymer chain, and preferably comprise organic macromolecules which are comprised of a first generally planar species connected by rigid linkers having a point of contortion such that two adjacent first planar species connected by the linker are held in a non-coplanar orientation. In a preferred arrangement, the angle made between said planar species on each side the point of contortion is a non-integral fraction of 360 degrees. Preferably, the pore size of the final PIM is controlled by the selection of a number of parameters; the functional group providing the point of contortion, the planar species, the molecular weight, and the optional substituents on the planar species. The PIMs materials may conveniently comprise functional groups on the planar species which are capable of providing polar, dispersive and charge transfer interactions between the planar rings and the target analyte. Thus, the PIMs material can be further adapted to provide a desirable pore size and/or chemical selectivity to improve affinity with the target analyte of choice.

The point of contortion may be any conformationally rigid group, such that there is substantially no rotation of the planar species about said group. This conformationally locked structure may be provided by fused rings, bridged structures or a spiro group, preferably a spiro group.

The intrinsic porosity of the polymer is provided by the conformationally locked structure, rather than weak intermolecular forces which are prone to decomposition at elevated temperatures.

In a preferred arrangement the polymer of intrinsic microporosity comprises a polymer, with a monomer repeat unit of Formula I

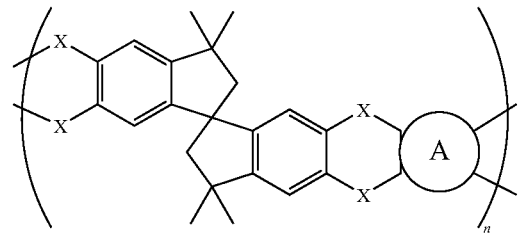

Formula I wherein A is one or more optionally substituted aryl, heterocyclic, cycloalkyl or bicycloalkyl rings, n is greater than 5, preferably 5 to 10000, and X may be selected from CH, $CH_2$, O, S, N or NH.

In an alternative arrangement there may be one or more independently selected monomer repeat units of Formula I within the trapping medium or final PIMs polymer, such as, for example, to form a co-polymer. The copolymer may be in the form of a random, block or any known statistical configuration of co-polymers. In a yet further embodiment there may be distinct regions or layers which are formed from different PIMs polymers of Formula I, or co-polymer, deposed on the element. In an alternative arrangement the trapping medium may comprise a co-polymer comprising one or more independently selected monomer repeat units of Formula I and one or more non-PIMs polymers.

Preferred optional substituents on the planar rings may be groups that are capable of undergoing electrostatic interactions, such as, for example, cyano, halo, haloalkyl, carbonyl, aryl, or heterocycles.

In a preferred embodiment ring A is selected so as to form an extended planar species, such as, for example, optionally substituted phthalocyanines, pyrroles and porphyrins.

In a preferred aspect the polymer comprises a monomer repeat unit of Formula II, which is a preferred example of Formula I;

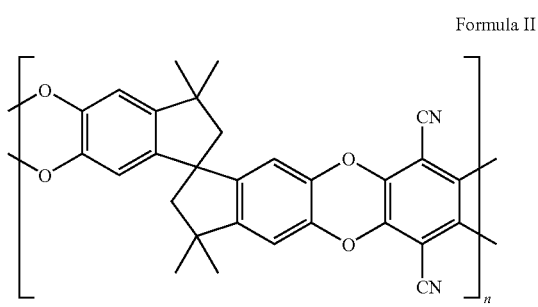

Formula II

The above polymer with a monomer repeat unit of Formula II has been given the non-IUPAC name of PIM-1 by McKeown et al.

In a further preferred aspect of the invention the polymer comprises a monomer repeat unit of Formula III, which is a preferred example of Formula I;

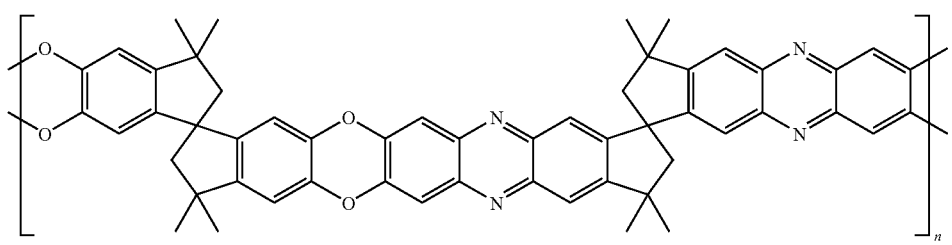

Formula III

The above polymer with a monomer repeat unit of Formula III has been given the non-IUPAC name of PIM-7 by McKeown et al.

The polymers of intrinsic microporosity (PIMs) may have a mean pore size in the range of from 0.05 nm to 100 nm more preferably 0.20 to 20 nm. The pore size of the PIM is controlled by the selection of; the functional group(s) providing the rigid framework, contorted linking groups which join segments of rigid framework together, any substituents on the polymer backbone which fill space; functional groups in the structure which influence intramolecular and inter-chain forces and the molecular weight.

Advantageously, the PIMs polymer provides a network of mutually interconnected pores into which and between which analyte molecules may percolate and, therefore, provides a multiplicity of sites at which the analyte molecules can be adsorbed. Therefore, the adsorption capacity of the PIMs for the analyte is much larger than that of a non-porous material such as silicon nitride. Advantageously, the PIMs polymer may have its pore size selected and surrounding chemical functionality selected such that molecules smaller than the target compounds are weakly adsorbed and molecules substantially larger than the target analyte are excluded from entry into the porous structure. In other words small molecules, such as, for example, diatomic gases, small hydrocarbons, may percolate through and large bulky, sterically hindered, molecules may not readily enter the porous structure and may therefore not be adsorbed to the same extent.

Advantageously, the chemical functionality surrounding the pores may be selected such as to selectively and reversibly adsorb the target analyte class by known physical and chemical interactions including hydrogen bonding, polar forces and dispersion forces. Thus, PIMs provide an improved porous adsorbent for use in a preconcentrator.

Preferably, the PIMs pore size may be equal to or slightly larger than the analyte of interest, but as the molecular chain of the PIMs material may also show some limited mobility a pore diameter slightly smaller than the analyte of interest may also be used. In a preferred option the PIMs pore size is a multiple between 0.6 and 10 times, preferably between 0.8 and 6 times, more preferably between 0.95 and 3 times the smallest diameter of the target analyte.

The polymers may be deposited on the element or preferably the heater, by any suitable method of deposition. Advantageously, the polymers are soluble in certain organic solvents and so may be conveniently applied, to the element or heater, in the form of a solution. This provides the advantage of achieving a highly reproducible and uniform thickness of PIMs coating, and furthermore it permits rapid manufacture of the units. It would be understood that the step of polymerisation of monomer units to form the PIM may alternatively be carried out on the surface of the element/heater. Preferably, the PIMs material is deposited in the polymerised form, which permits purification of the PIMs prior to deposition.

Preferably, the polymer is deposited onto the element or heater by any liquid deposition technique, such as, for example, brushing, spin coating, dipping, curtain coating, spray coating, inkjet printing, electrospray coating or Plastisol® coating.

The PIMs coating may cover part, substantially all or all of the surface of the element or heater. In one embodiment, the PIMs coating may be used in combination with existing preconcentrator trapping media.

The polymer may be deposited on the element or heater, either by stepwise layering or in a one-step procedure to any desirable level of thickness. The actual thickness of the polymer will preferably be selected to allow sufficient surface area of polymer to be achieved and ensure a low thermal mass such that, in use, rapid and uniform heating of the polymer can be achieved. In a preferred arrangement, the polymer is deposited to a thickness of less than 100 microns, more preferably a thickness in the range of from 0.01 microns to 100 microns, yet more preferably in the range of from 0.01 microns to 0.5 microns.

The efficiency of the preconcentrator may be controlled by altering the surface area of trapping medium i.e. altering the amount of PIMs polymer that is available to trap the analyte, which may in part be controlled by the physical dimensions of the element or heater. In a preferred arrangement the deposited polymer layer has a surface area of at least 50 $m^2/gm$, more preferably a surface area in the range of from 800-1200 $m^2/gm$.

The affinity ratio is particularly difficult to measure and may not be appropriate for some materials. The figure of merit (Q) may provide a very basic method of measuring efficiency, which is defined as:

$$Q = \frac{m_{20}^2}{M \cdot m_{200}}$$

where $m_{20}$ is the mass of analyte adsorbed by mass M of the preconcentrator material (polymer) at 20° C. in equilibrium with the analyte at a concentration of 0.1 of its SVP at 20° C., and $m_{200}$ is the mass of analyte retained, by the same mass M of preconcentrator material in equilibrium with the same vapour concentration at 200° C. A desirable figure for Q is >1, and more preferably in the range of 100 for very high affinity materials.

The preconcentrator defined in the invention may be used in an integrated chemical detection device, such that trapping and analysis/detection is performed in one dedicated piece of equipment. Conveniently, for the rapid detection of analytes in real-time, the sampling platform may form an integral part of a detector, wherein said chemical detection device is suitable for collecting and detecting said analyte. This provides for a portable system, which can be used to analyse components in the environment of choice.

In an alternative embodiment, the preconcentrator may be used in a system where collection and detection of the analyte are performed in separate steps. In the first stage the preconcentrator will be located in a collection device, to allow adsorption of the analyte. The preconcentrator may be transferred to a dedicated analysis machine, such that the final steps of desorption and detection may be performed in an alternative location, such as in a laboratory.

Typically, in portable chemical detector preconcentrators, the element bearing the trapping medium is a heater, thereby avoiding the use of a separate heater. The heaters are designed to provide a particular operating temperature and/or fit into an existing particular device. Furthermore, heaters are typically of a uniform thickness, which may cause differences in heat flow or resistance at various points in the heater. This variation may give rise to hot-spots and consequently poor heat distribution on the surface of the heater. A yet further consideration is that hot-spots caused by necking or thinning of the heater may ultimately reduce the life expectancy of the heater, particularly as a result of repeated heating and cooling cycles.

A yet further problem with prior art preconcentrators that are miniaturised for use in portable detection systems is their low efficiency. This is due to a low surface area of the preconcentrator, in particular the trapping medium area. This reduction in trapping medium area reduces the overall efficiency of the detection system.

Uniform temperature distribution across the entire surface of the sampling platform, which in a preferred embodiment comprises the heater with a coating of trapping medium thereon, is most important during the desorption phase, which is when the heater is activated to release the trapped analyte from the trapping medium. In order to achieve a uniform, more steady state temperature distribution in the heater, the structure of the heater is preferably optimised to balance heat generation and heat losses. Further factors which are important to achieving appropriate performance are efficiency (i.e. heat input required to achieve a given temperature) and the speed of heating and cooling. The rate of cooling is determined by the heat loss from the heater and is ideally balanced with efficiency.

The time taken to reach a steady temperature under open loop control conditions is determined by the thermal time constant of the system which is minimised when heat losses are large.

The use of a closed loop control system can enable more rapid heating, but a design of heater which achieves uniform temperature distribution in the steady state may not achieve uniform temperature distribution during rapid heating due to imbalances between heat generation and thermal mass.

According to a fourth aspect of the invention there is provided a chemical detection system for detecting a low concentration of an organic analyte, said system comprising a means for collecting a sample of gas comprising the organic analyte to be detected, a preconcentrator device as hereinbefore defined, and a detector suitable for detecting said organic analyte. Preferably the chemical detection system is a hand-held or portable chemical detection system. In a preferred embodiment the preconcentrator forms an integral part of the detector.

The detector may be any suitable detector for detecting the target analyte; suitable detection techniques may be, for example, ion mobility spectrometry, mass spectrometry, UV, IR, gas chromatography, or GC-MS. The role of the detector is to measure the presence of the analyte and, depending on the detector, the quantity and the identity of the analyte that is released from the preconcentrator may also be determined.

According to a further aspect of the invention there is provided a method of preparing a micro machined heater as hereinbefore defined comprising the steps of forming the pattern of the heater configuration by deep reactive ion etching of a supported silicon layer, such as for example a silicon layer on a glass carrier.

A yet further aspect of the invention provides a method for preparing a preconcentrator comprising the step of depositing a polymer of intrinsic microporosity onto a heater according to the invention. Preferably the deposition comprises the steps of i) forming a solution of the polymer in a solvent ii) contacting the polymer solution to said heater and iii) evaporating the solvent to produce the membrane, optionally repeating steps ii) and iii) to achieve the desired thickness of polymer. Preferably the heater has an open lattice arrangement. Conveniently, the PIMs material only deposits on the exposed surfaces of heater and does not completely fill the voids in the lattice such as to prevent a through flow of air.

The solvent may be an organic solvent, preferably one selected from polar, aromatic, halogenated, or halogenated aromatic solvents, such as, for example, THF, methanol, dichloromethane, chloroform, etc. Conveniently, the solvent is selected such that it has a boiling point at atmospheric pressure between 40° C. and 250° C., preferably between 80° C. and 210° C., more preferably between 120° C. and 190° C.

A further advantage of processing the deposition using solvents is the ability to form thin films. Advantageously, the thin film retains the high internal free volume, providing desirable vapour permeability. This allows for the rapid and effective capture and release of the analyte from and to a gas stream and in turn allows for the high flow rates of a carrier gas, comprising a target analyte, to percolate through the PIMs' network. The carrier may, for example, be air containing airborne particulates, vapours or aerosols.

According to further aspect of the invention there is provided a method of preconcentrating an organic analyte comprising the steps of i) placing a preconcentrator as hereinbefore defined in the path of an inlet gas flow to allow adsorption of the target analyte to occur ii) causing an increase in temperature of the polymer of intrinsic microporosity, to desorb said analyte. In one embodiment a chemical detection system may allow adsorption by continually cycling a steady stream of a gas. Alternatively, the sampling may be carried out over a defined period of time or after a fixed volume of carrier gas has been passed over the preconcentrator.

There is further provided a method of detecting an organic analyte comprising the steps of preconcentrating an analyte as hereinbefore defined, and passing said desorbed analyte into a detector. After a predetermined time, the heater will rapidly increase the temperature of the PIMs causing the analyte to be physically desorbed. The desorbed analyte may be swept to the detector by any suitable means, such as, for example, by an inert carrier gas, reduced pressure or simply by convection. There may optionally be a delay between steps i) and ii) to allow sufficient build up of analyte, or to allow the adsorption step and desorption/detection steps to be carried out in separate stages, or separate locations.

The PIMs structure is particularly suited to reversibly adsorbing organic analytes, preferably aromatic compounds or compounds which possess a molecular electric quadrupole moment. The PIMs material has shown particular advantage for reversibly adsorbing electron deficient aromatic compounds and especially compounds which comprise one or more nitro or nitroester groups, such as, for example, nitrotoluene, dinitrotoluene or trinitrotoluene.

The PIMs structure provides significant advantage over existing preconcentrator trapping mediums, because electron deficient aromatic compounds are difficult to desorb from commercial preconcentrators, without causing thermal decomposition of the trapped medium or in certain cases the analyte if high temperatures are used.

According to a further aspect there is provided the use of a polymer of intrinsic microporosity for reversibly adsorbing an organic analyte in a preconcentrator device, preferably for use in a portable chemical detection system.

A preconcentrator which is intended for preconcentration of trace quantities of vapour, and delivery of this vapour to a detector, should preferably satisfy a number of requirements. These will contribute to achieving a high degree of effectiveness in improving the detection limits for target compounds while providing a preconcentrator which is practical in operation.

Target compounds for detection may be present at extremely low vapour concentrations, and therefore a large volume of air or input gas stream must be sampled in order that the sampled gas stream contains a total quantity of analyte sufficient to register on the detector. Furthermore, depending on the application of the detection equipment, it is often desirable to achieve detection of the target compounds, if present, in a short time period so that appropriate action may be taken, or to measure a large number of samples in a limited period.

It is desirable that a preconcentrator should allow a large flow rate to be effectively sampled, without undue loss in the capture efficiency of the vapour, preferably without an excessive input of electrical power. It is desirable to provide a structure where the target analyte vapour passes in close proximity to the trapping medium, such that it may be extracted from the input gas flow and trapped within the short residence time of the input gas flow in the device. The use of a PIMs coated heater according to the invention provides a trapping medium which largely satisfies all of these requirements.

In the desorption phase of preconcentrator operation, the preconcentrator is heated to release the trapped analyte vapour into a small volume of carrier gas, at significantly higher concentration than was present in the input gas stream. The rate of desorption of the analyte vapour is dependant on the nature of the target analyte and of the trapping medium. The rate of desorption is also increased by increasing the temperature of the trapping medium, the temperature range needs to be selected so that the temperature does not cause undesirable degradation of the analyte, but still enables rapid desorption.

To achieve a high concentration of analyte vapour in the carrier gas, the analyte is preferably released from the trapping medium very rapidly. In order to achieve this, the preconcentrator structure is preferably capable of being heated very rapidly and very uniformly over a large temperature interval. The use of an isopotential heater as hereinbefore defined may reduce the heating time and provide a uniform heat distribution across the entire surface of the heater, and therefore the PIMs coating, to aid the rapid desorption of trapped analyte. Preferably the time taken to heat the trapping medium up to the required desorption temperature is less than a second.

The preconcentrator is desirably heated using only a small amount of electrical energy. A low energy requirement in this step and in the sampling phase of operation contribute to providing a preconcentrator which may be operated on battery power where mains power is not available, and to providing a preconcentrator which may be used in portable or handheld equipment. The use of a MEMS heater as hereinbefore defined will readily permit lower energies to be used as the heating will be more electrically efficient, i.e. a reduction in hot-spots due to high resistance structures.

The preconcentrator heater according to the invention provides a device which achieves improved preconcentration efficiency by possessing a heater which is capable of very rapid, very uniform temperature rise with a small input of power. The PIMs trapping medium provides the advantage of being an organic polymer with a high affinity for organic molecules and which is thermally stable up to unexpectedly high temperatures, which is desirable in preconcentrator devices. A yet further benefit is that due to the intrinsic shape of the heater structure, the temperature of the preconcentrator is returned rapidly towards the ambient temperature, in preparation for the next sampling phase of operation.

Thus the heater according to the invention in combination with a PIMs as part of a trapping medium, allows for a high surface area of trapping medium to be available for trapping analyte, but which surface area can be rapidly heated in less than a second, so as to be useful for feeding the concentrated analyte into a subsequent detection system. Furthermore, the PIMs trapping medium is thermal stable, thus allowing routine i.e. continued temperature cycling during operating conditions.

The preconcentrator, particularly the trapping medium, should preferably be selected so as to allow rapid diffusion of the analyte when released from the trapping medium so that it may be delivered to the detector in a concentrated burst. A further advantage of this invention is to provide a preconcentrator having a thermally stable trapping medium with a trapping strength and capacity suitable for preconcentration of a target analyte. A yet further advantage is to provide a preconcentrator with its trapping medium such that release of desorbed analyte into a carrier gas stream can occur rapidly.

DETAILED DESCRIPTION OF THE INVENTION

In one embodiment, the heater is made by Deep Reactive Ion Etching a silicon substrate, which is further bonded to a glass substrate. The glass substrate provides structural support to the heater; clearly other means of support may be envisaged. Through-holes are provided in the glass substrate, such that, in use, fluid is able to flow through both the lattice structure of the heater and the supporting glass substrate. The trapping medium is formed by coating the heater with at least one polymer of intrinsic microporosity. In use the heater structure is heated, by joule-heating, by applying a voltage across the heater. It is highly desirable to desorb the analyte over a very short time period, preferably less than a second.

This allows the preconcentrator to absorb the analyte from a comparatively large volume of sample, and release it in a short pulse at a higher and hence more easily detectable concentration. Conveniently, enhancement of vapour detection sensitivity is increased by at least 1-3 orders of magnitude, which allows for the analysis of analyte present in the concentration range of parts per billion or parts per trillion.

A particular organic analyte of interest is TNT, which is a widely used military and commercial explosive. Trace detection of TNT is of key importance to operations such as minefield clearance. Detection of TNT is made difficult by the small concentrations of vapour normally encountered; although the saturated vapour pressure of TNT at ambient temperature is a few ppbv, the vapour concentration in the vicinity of an unexploded mine buried in soil may be several orders of magnitude lower than this. The use of the polymer of intrinsic microporosity in a preconcentrator is particularly useful for creating a miniaturised and portable TNT vapour detection system. Trace detection of analytes in quantities of the order of a few nanograms or fractions of a nanogram has been achieved, as outlined in the experimental section below.

Embodiments of the invention are described below by way of example only and in reference to the accompanying drawings in which.

Figure 3A:
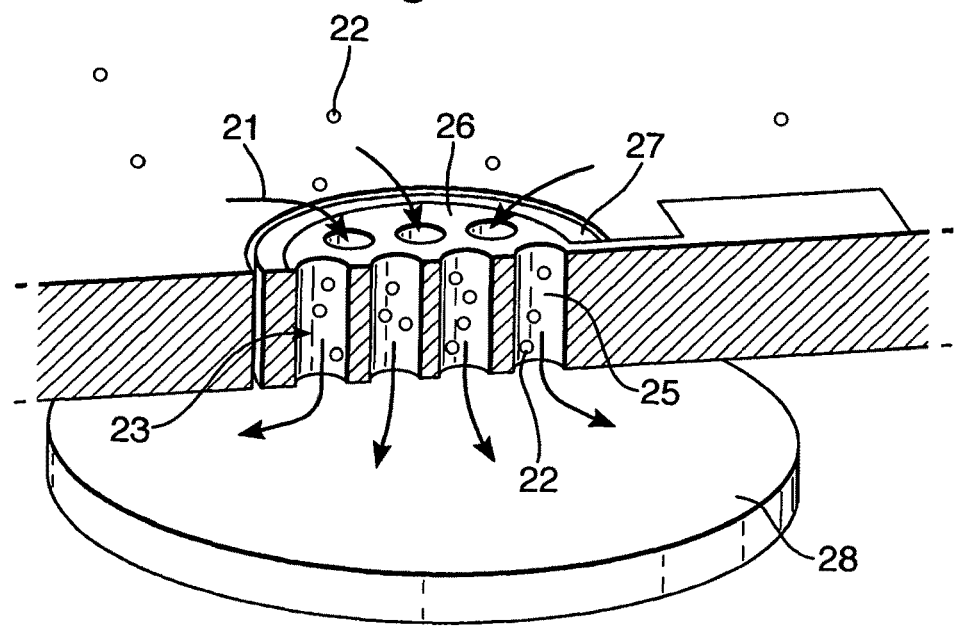

FIGS. 3a and b show a schematic diagram of a preconcentrator, which uses a shuttered means of controlling the analyte to a detector.

Figure 4:
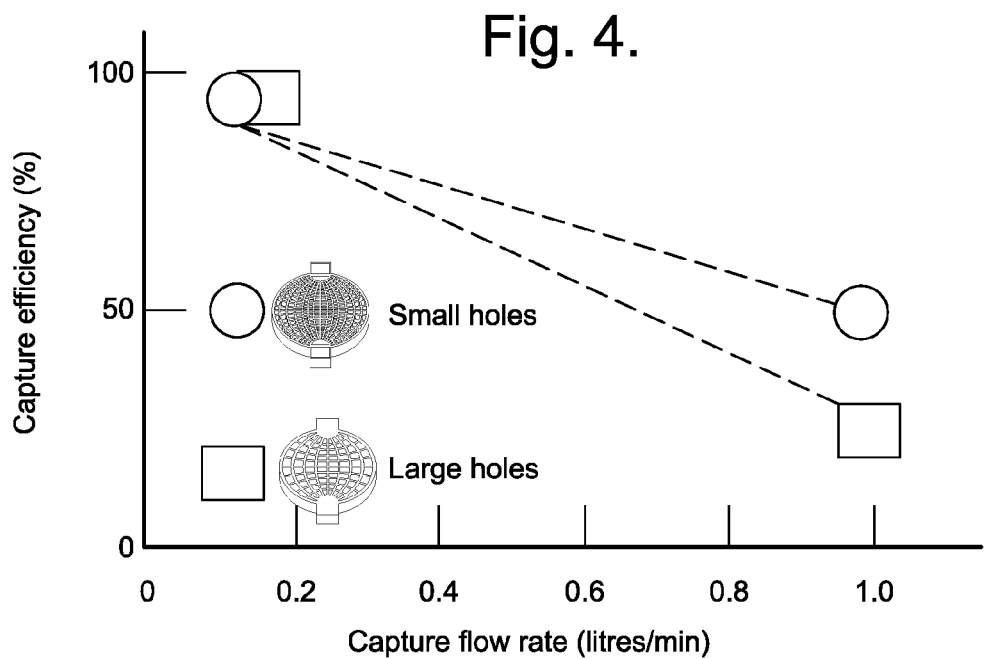

FIG. 4 shows a graph of the effect of the hole size in the heater and its effect on capture efficiency.

Figure 5:
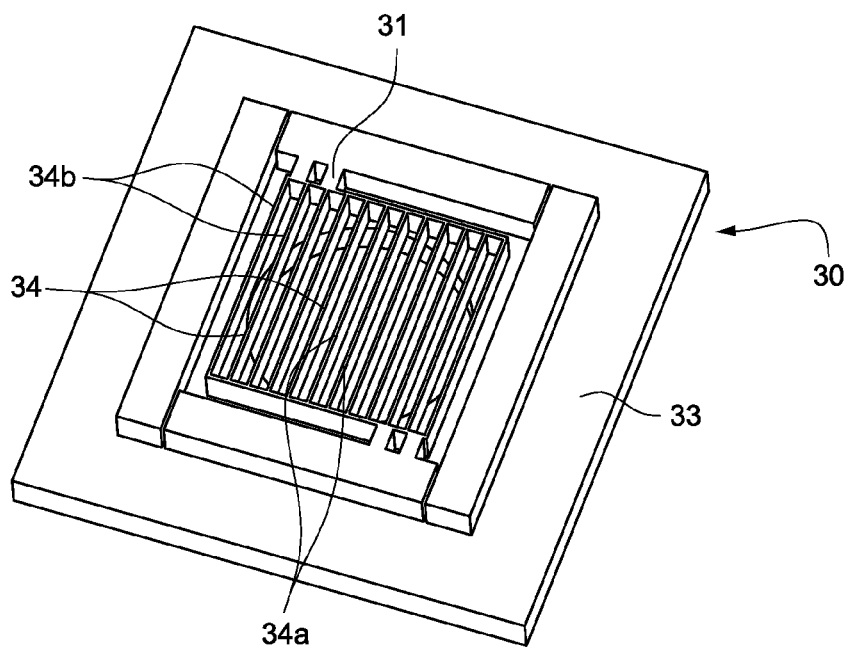

FIG. 5 shows a configuration of a heater which does not possess an isopotential structure, wherein the electrically conducting paths have different resistances, which gives rise to a non-optimised heating profile.

Figure 1A:
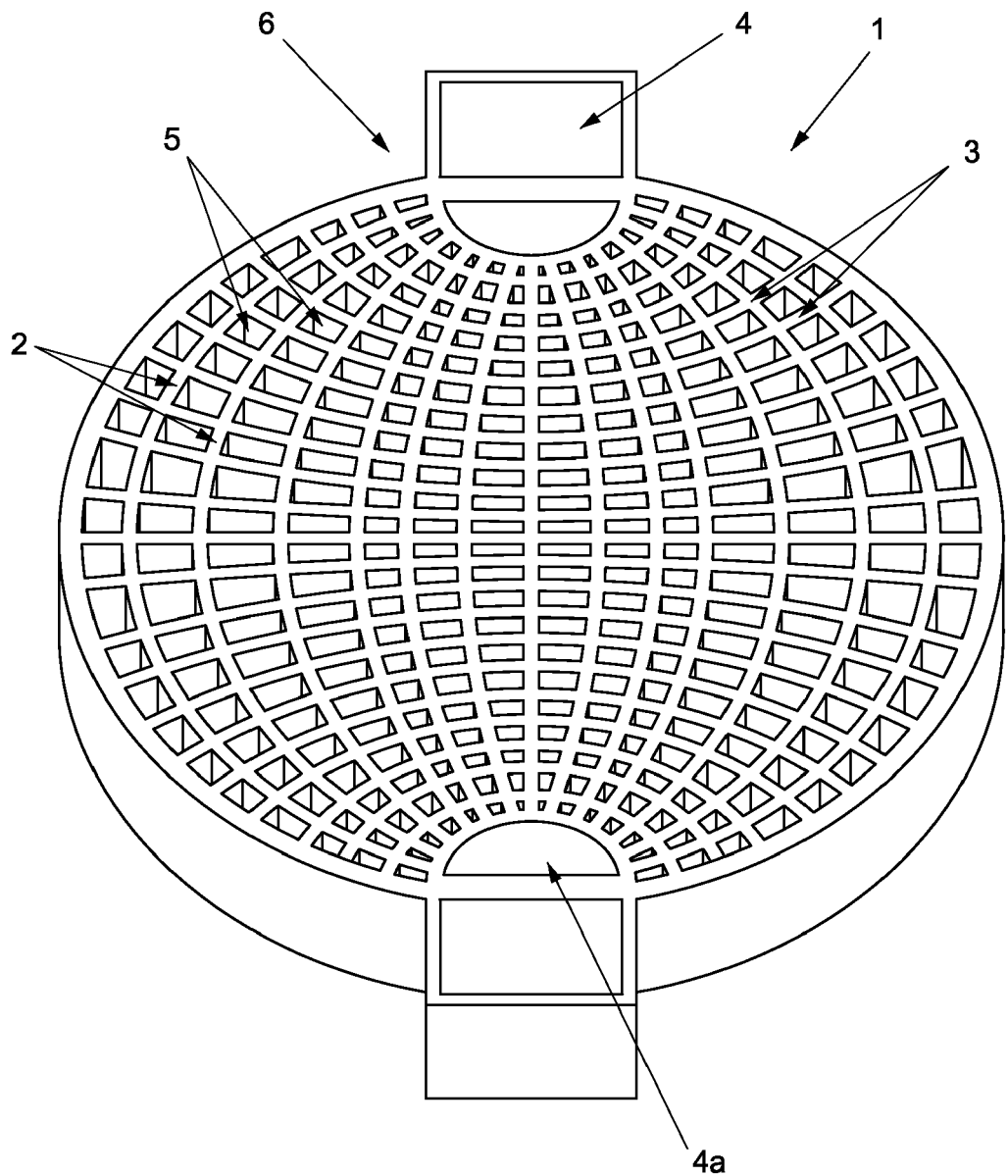
FIGS. 1a and 1b show a photograph and plan view of a heater respectively.
Figure 1B:
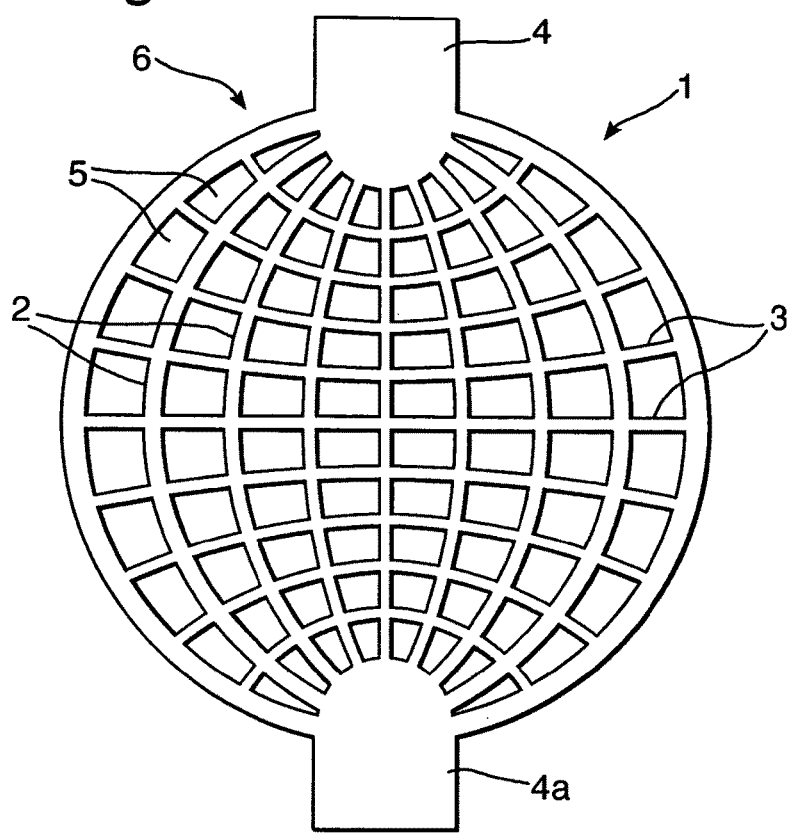

Turning to FIGS. 1a and 1b, the heater 1 is substantially circular and may be constructed from any suitable conductive material. The shape of the heater is defined by a series of conductive bars (preferably in the form of arcs) 2, projecting from the two junctions, contact areas 4 and 4a, which drive the potential difference across the heater 1. The conductive bars (arcs) 2 are strengthened by a plurality of intersecting struts (conductive crossbars) 3, which are also arcuate. The conductive bars 2 and conductive crossbars 3 are preferably formed from one piece of conducting substrate material, by any known method. At the point of intersection of two conductive bars 2 and two conductive crossbars 3, a through hole 5 is formed, which allows for a rapid through-flow of the carrier fluid comprising the target analyte. The top surface 6 of the heater (conductive bars 2 and conductive crossbars 3) and the internal cavity of the through-hole 5 may be coated with a polymer of intrinsic microporosity (not shown). Increasing the through flow of the inlet gas may allow more of the target analyte to be adsorbed onto the surface of the PIMs material.

Figure 2:
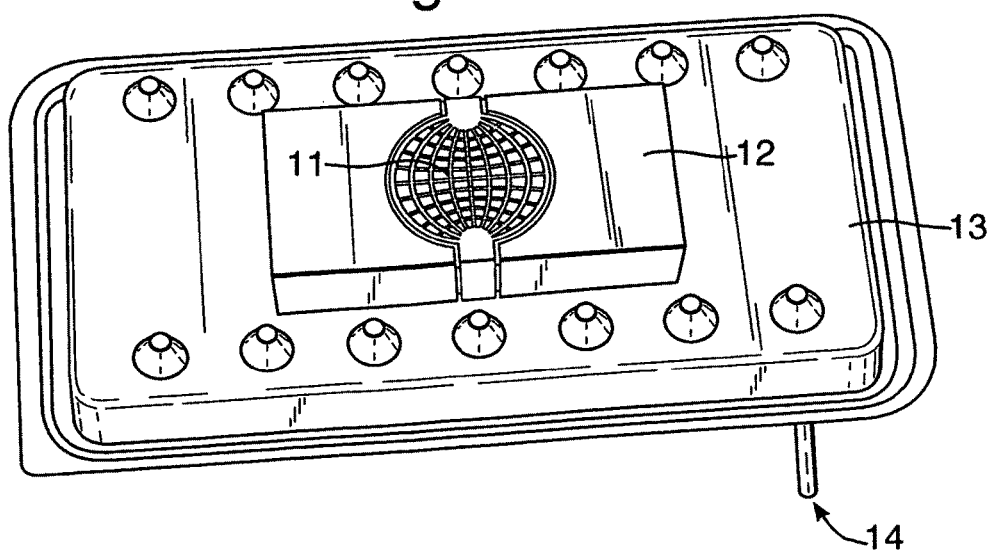
FIG. 2 shows a plan view of a heater embedded into a chip assembly ready for mounting onto a circuit board.

FIG. 2 shows a heater 11, as shown in FIG. 1, encased by a support 12 which is mounted on a chip 13. The pins 14 may be connected to a circuit board, by any conventional means, and may provide the electrical potential to heat the heater 11.

Figure 3B:
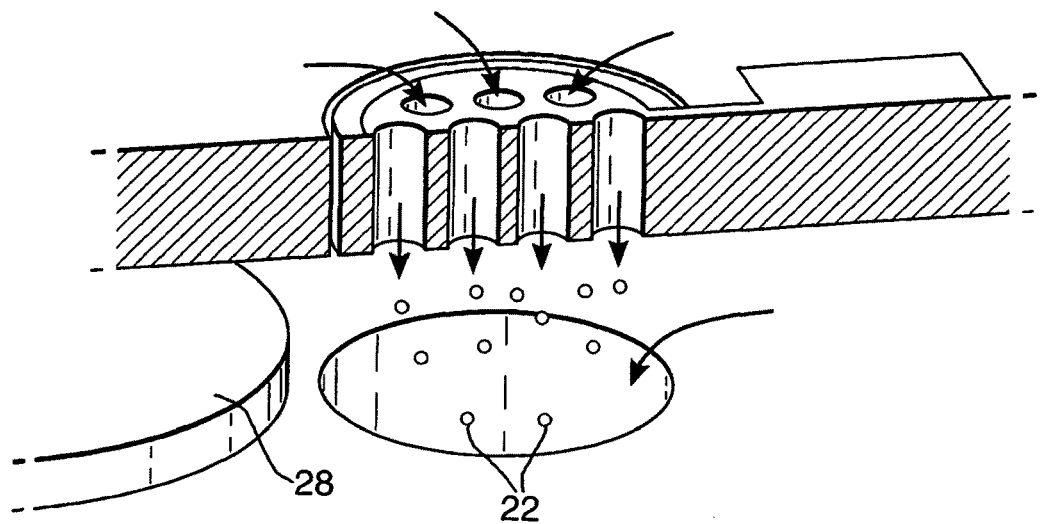

FIGS. 3a and 3b show a cross section of a schematic diagram of one particular arrangement of use for the preconcentrator 23. The upper surface 26 and the walls 25 defining the cavities, created by the struts and arcs in FIG. 1, are coated with a uniform layer of the PIM material 27.

In the sampling phase (FIG. 3a), a large volume of vapour 21 comprising the trace concentration of analyte is flowed through the pre-concentrator and the analyte 22 is trapped in the PIMs material 27. During the desorption phase (FIG. 3b), the trapped analyte 22 is released by rapidly heating the heater 23, typically to at least 200° C., in preferably less than one second. The released analyte 22 is transported to the detector (not shown) in a minimum volume of an inert carrier gas. In one arrangement, there may be a shutter 28, which can be opened to allow the flow of the analyte 22, in the inert carrier gas, to progress into the detector. Clearly it would be readily appreciated that there are many methods of controlling the flow of a desorbed analyte into a detector, such as, for example a shutter mechanism as shown or the physical movement of the preconcentrator from a collection region to an output region housing the detector.

FIG. 4 shows a graph of the effect of large and small holes and the flow rate and their effect on the capture efficiency of analytes. To consider the effect of the hole size, the holes may be considered as an array of micropipes (channels of radius=r) through a substrate of thickness L. The principal aspects of preconcentrator performance may be estimated by the following relationships and approximations:

The flow of sampled gas through the structure is given by the Poiseuille flow formula:

$$Q = \Delta P \cdot \pi \cdot r^2 \cdot A \cdot F / 8 \cdot L \cdot \mu$$

Where Q is the rate of fluid flow, $\Delta P$ the pressure drop, A the area of the substrate, F the fill factor of channels through the PC structure and $\mu$ the viscosity of the gas stream.

A large volume of gas may be sampled rapidly and at low pressure drop (and therefore energy input) by choosing large values of r and A, and a small value of L. However, selection of r and L is constrained by the requirement to efficiently trap analyte passing through each channel. The trapping efficiency may usefully be approximated as:

$$E_t = 1 - (1-S)^{(d/r)}$$

Where S is a sticking coefficient for the analyte on the trapping surface, and d is the diffusion distance of the analyte:

$$d = (D \cdot t)^{0.5}$$

where t is the transit time of gas through the channel and D is the diffusion coefficient of the analyte. Preferably, S is close to 1, and efficient trapping of the analyte can be achieved if d is comparable with or greater than r.

FIG. 5 shows a non-optimised heater which has been simulated in an electrical modelling program. The structure is of the flow through type, where the flow through structure is mounted by contact areas 31 which are located at either side of the structure 30 to connect to a carrier substrate 33. The heater is defined by a series of conductive bars 34, which are all the same thickness but are of varying length between the two electrical contact areas 31, hence their respective resistances between the two electrical contact areas 31 are different. It has been shown by heat flow simulations, that a steady state temperature distribution cannot be achieved in such a structure when heated by passing current through the conductive bars 34.

The central conductive bars 34a are hotter than the outlying conductive bars 34b, and so offer different levels of electrical and thermal resistance, resulting in non-uniform heating and in non-uniform heat loss. This problem of non-uniform heating has been overcome by using an isopotential structure such as shown in FIG. 1. Clearly the square shaped heater in FIG. 5 may be optimised to that of the invention if the bars 34 are all configured such that they have substantially the same resistance and each bar 34 originates from the contact areas 31.

Experimental
Preconcentrator Structures

Tests have been carried out on two types of preconcentrator structures, a granular alumina support coated with a PIMs material with an external heater (one which is not in direct thermal contact with the PIMS) and a silicon heater with an isopotential configuration coated with a PIMs material. Each preconcentrator was subjected to a known amount of either DNT or TNT vapour, the preconcentrator removed and then placed in a separate machine, a TD-GC-MS (Thermal Desorption-Gas Chromatography-Mass Spectroscopy) detector system, to accurately assess the preconcentrator performance.

The micro machined silicon heater was optimised to allow rapid and uniform heating with a low energy requirement. These requirements led to a heater with the structure of a perforated disc, 5.8 mm in diameter, 525 microns thick and having a surface area of 100 mm$^2$ through which the sampled gas can flow.

The ability of a PIMs coating to trap and release TNT or DNT, and the thermal stabilities of the PIMs heater system, were assessed using TD-GC-MS. The TD system was a Perkin Elmer Turbomatrix ATD-50 attached to an Agilent 6890A GC with a 5973N mass spectrometer using EI ionisation. The cold spot of the turbomatrix was operated at −20° C. during desorption of the samples and rapidly heated to 225° C. at 40° C./min upon injection into the GC.

Coating an Alumina Granular Support and the Silicon Heater

The PIM materials PIM 1 and PIM 7 were dip coated onto alumina granular supports. Polymers PIM1 and PIM7 were coated onto calcined alumina powder (3 µm diameter) at a loading of 3.7 wt % of polymer in solution of chloroform. This loading is equivalent to a 0.37 µm thick uniform coating. This coating thickness was consistent with electron micrograph images of cleaved sample devices.

For the heater coating, the micromachined silicon heater was dip-coated in the PIM material from 2.6% solution in dichlorobenzene. The removal of solvent furnished a heater with a 110-120 µg of PIM, equivalent to a uniform coating about 100 nm thick. The mean pore size for the PIM polymers is estimated from low temperature nitrogen sorption to be in the range of 5-7 nm. This coating thickness was consistent with electron micrograph images of cleaved sample devices.

Thermal Stability

The thermal stability of each preconcentrator surface was assessed by heating the material in a helium flow at 150° C., 175° C., 200° C., 225° C. and 250° C. using the above thermal desorption unit. Mass analysis was used to identify whether there were any products of thermal desorption of the PIMs, which could interfere with identification of target analytes, results shown in Table 1 below.

TABLE 1

Thermal stability of candidate preconcentrator surfaces.

| | Alumina PIM1 | Alumina PIM7 | Si heater PIM1 | Si heater PIM7 |
|---|---|---|---|---|
| Thermal stability/225° C. | Good | Good | Good | Good |

The polymer materials PIM1 and PIM7, when deposited on either granular alumina or a silicon heater, showed no signs of degradation under the thermal stability assessment conditions. It was found on initial heating of the polymer, however, that some side products as a result of the synthesis of the polymer, were present on the PIMs and were subsequently released to the detector. It may therefore be desirable to precondition the PIMs layer on the heater, prior to use, to remove adventitious contaminants.

Alternatively, higher purity polymers may also be used. The thermal testing showed that both PIM1 and PIM7 were stable up to temperatures of 250° C. in helium. This is highly desirable, as many organic network polymers will degrade significantly when heated to such high temperatures. The increased likelihood of thermal degradation of organic polymers limits their use on preconcentrators and hence, thermally stable inorganic network layers are favoured. PIMs polymers are particularly suited to continual heating and cooling cycles due to their high thermal stability.

Trapping and Release on an Alumina Granular Support

The trapping efficiency of the PIMs materials were determined by exposing ca. 75 mg samples of PIMs on an alumina support, contained in glass tubes, for two minutes, to a TNT vapour generator. The vapour generator operated with a 100 mL min$^{-1}$ output in nitrogen which delivered 20-40 ng of either TNT or DNT (depending on the quantity of material in the vapour generator) onto the sample under investigation.

The release was measured using TD-GC-MS. The samples were loaded into tubes for desorption. The correct gas flow through each packed tube was verified with a flow meter before testing. Control experiments were carried out using Tenax TA tubes (60/80 mesh) under the same conditions. The tubes containing the alumina:PIMs:adsorbed TNT or DNT, were then analysed using TD-GC-MS. All measurements were carried out in triplicate. Concentrations were determined using external standards injected onto Tenax. Calibration was determined from the peak area of selected ions using a three point linear calibration forced through the origin. The tubes were desorbed onto the cold spot of the TD unit at 225° C. at a flow rate of 45 mL min$^{-1}$ of helium for 6 minutes.

TABLE 2

TNT/DNT trapping and release performance of candidate polymer surfaces.

| Alumina | PIM1 | PIM7 |
|---|---|---|
| TNT trapping efficiency | 100% | 100% |
| TNT recovery/225° C. | <10% | 62% |
| DNT trapping efficiency | 97 | 100 |
| DNT recovery/225° C. | 88 | 59 |

Tests with PIM1 and PIM7 on a granular support indicated that both polymers provided highly efficient trapping of either DNT or TNT vapours, as shown in Table 2, above. However, PIM7 was able to release more of the trapped vapour compared to PIM1, for TNT.

In the experiment where PIM1 is deposited on an alumina support, there is a decreased amount of desorption of TNT, compared to the PIM7 coating on the same support, this is due to the partition coefficient being very large, i.e. the analyte, TNT, is very strongly absorbed on the PIM 1. It would be readily understood by the skilled man that reduction of the retention time, of TNT on PIM 1, may be afforded by, using a shorter vapour path through the preconcentrator, or by increasing the relative volume of gas, and/or by reducing the relative volume of PIM 1. These parameters are realised in physical dimensions of the coated silicon structure, described below, which is presented as a perforated thin disc with a more open structure.

When a carrier gas is subjected to preconcentrating, the gas is passed over the preconcentrator structure. In a first phase there is absorption of the analyte from the gas stream and in a second phase there is desorption from the preconcentrator. The desorbed analyte will then be carried by a separate inert gas stream, at a higher temperature, into the detector.

In the situation of the TNT retention on the PIM 1 material coated on alumina, there are several features which may contribute to the hold-up of the analyte vapour:
  A small free volume of gas between the grains of alumina powder
  A (relatively) large surface area of powder, and hence large exposed volume of PIM 1

A tube through which the gas flows, which is much longer than the distance between the alumina particles.

These features provide is an environment in which the analyte is absorbed at the upstream end of the tube packing. At low temperature, there is no bleed-through of analyte. When the temperature is raised, a small amount of the analyte is desorbed—but not fully. Rather, the heating causes a change in the partition coefficient of the analyte between the gas phase and the PIM material. The above three effects dictate that the tube and packing now behave effectively as a chromatography column; there is constant equilibration between the gas stream carrying some concentration of analyte, and the PIM. The analyte vapour moves through the tube in a retention time t, where $$t = t_M \cdot (1 + k)$$

where $$k = \frac{V_s \cdot C_s}{V_M \cdot C_M}$$

In which $t_M$ is the time taken for the gas stream to transit the tube, $V_s$ and $V_M$ are the volume of the stationary (PIM) phase and the mobile (gas) phase in a unit length of tube, and $C_s/C_M$ is the partition coefficient of the analyte between the PIM and the vapour phase. Clearly, for strong absorption of the vapour onto the PIM, and for higher loadings of PIM and less gas volume between the packing particles, t can become very long.

The efficiency of this separation is quantified by the number of theoretical plates provided by the tube. The well known and understood principles of chromatographic plate theory and rate theory describe how to measure the number of theoretical plates corresponding to a tube, and hence the length of tube which corresponds to one theoretical plate (the HETP). The theories also provide descriptions of the release profile of vapour from such a column. The retention time may be reduced by raising the temperature, and thereby altering the partition coefficient—but this is limited by the eventual decomposition of the analyte or PIM at high temperature.

Therefore the person skilled in the art of chromatographic plate theory would readily be able to establish the perquisite parameters for any given PIMs membrane, on any dimension of preconcentrator support or heater, for use with any analyte of interest. Clearly, different analytes will have different partition coefficients (at any given reference temperature) and decomposition temperatures.

Therefore the instance of excessive retention of TNT on PIM1 on a granular alumina support, is merely due to the physical dimensions of the preconcentrator, and routine experiment would readily provide the desired physical dimensions, such as surface area, thicknesses, etc.

The PIMs polymers provide excellent results, for the detection of aromatic analytes, when used as part of MEMS scale preconcentrator, which is in part due to the PIMs possessing high partition coefficients.

PIMs Coated Directly onto a Silicon Heater

The PIM 1 and PIM 7 polymers were applied, using solvent cast coatings, on to the surface of a silicon heater, as described earlier.

The preconcentrator structure was first exposed to the outlet of the TNT vapour generator running under the same conditions as for the granular support test conditions, as detailed above. After exposure to the vapour, it was transferred to the glass tube assembly for thermal desorption analysis of the trapped vapour. A blank, uncoated silicon heater was tested as a control alongside samples coated with PIM1 and PIM7 respectively. The trapping efficiency and recovery of TNT from each sample is shown in Table 3.

TABLE 3

Recovery of absorbed TNT and DNT vapour from coated MEMS preconcentrator elements. (n/a—not determined)

| Coating on MEMS Silicon element | No coating | PIM1 | PIM7 |
|---|---|---|---|
| TNT trapping efficiency | n/a | 100% | 100% |
| TNT recovery/225° C. | 10% | 72% | 60% |
| DNT trapping efficiency | n/a | 66.6% | 21.8% |
| DNT recovery/225° C. | 10% | 46% | 33.0% |

Tests with PIM1 and PIM7 on the silicon element indicated that both polymers provided highly efficient trapping of either TNT or DNT vapours.

The above table shows that the heater without a PIMS coating may be used for preconcentration albeit at a reduced level of efficiency.

Experiments have also revealed that altering the size of the holes in the open lattice heater, as shown in FIG. 1, alters the capture and release efficiency. There is a general trend that for higher flow rates lattices with smaller hole sizes capture a greater amount of the target analyte.

Experiment to Examine Effects of Hydrocarbons on Capture Efficiency

A micromachined heater as previously described above with a PIM1 coating was subjected to petrol vapour then TNT vapour, to assess the effect of contamination. The capture and release of target analytes in real time environments, will probably involve other contaminants being present. A good source of a wide spectrum of hydrocarbons is RON 95 petrol. The effect of contamination, by petrol, on the capture/release efficiency of a preconcentrator, coated with PIM1, was determined by:

Active sampling of the headspace vapour of RON 95 petrol (50 mL)@1 L/min for 2 min Active sampling of TNT from a vapour generator@1 L/min for 2 min Desorb the analyte in TD-GC-MS After the desorption phase the results showed evidence of the part of substituted benzene derivatives and other volatiles present in the RON 95 petrol. Also present was the TNT, which had a 78% capture/release efficiency. Therefore even with the presence of a highly complex hydrocarbon source, such as petrol, the PIMs coating was still able to pre-concentrate the TNT vapour.

The PIM1 and PIM 7 when coated onto the micromachined silicon support show a highly efficient release of the target analyte vapours, when compared to coatings on a granular support. The silicon heater is essentially a perforated thin disc with a more open structure than the granular support. In the heater structure there is little opportunity for successive re-equilibration between vapour and PIM; the structure will have little capability to separate different absorbed materials, the disc will possibly only possess 1 theoretical plate.

There is a further advantage when the PIMs materials are in direct and intimate contact with the heater, which is that the primary means of heating is via conduction. This allows for quicker heating due to less thermal lag. Preferably the PIMs polymer is directly coated onto a heater.

Facile permeation of small organic molecules through the rigid disordered structure of these polymers is evidenced by their high absorptive power for small aromatic compounds such as phenol, while dyes with molecular diameter ~1 nm are excluded from the polymer. This allows a PIMs coated preconcentrator with a suitable porosity, to allow the adsorption of small organic compounds and ignore larger background components. The MEMS (Micro-Electro-Mechanical Systems) scale silicon element as hereinbefore defined supports a lower mass of coating, and provides a less serpentine flow path than the powdered alumina support. PIMs structures which interact more strongly with TNT or DNT vapour are correspondingly advantageous on the thin, lower surface area, micromachined preconcentrator. The trapping efficiency and release rates may also be influenced by the flow rates, instrument geometry and desorption temperatures that are used.

The PIM materials offer a family of stable, high surface area absorbents whose structure may be chemically altered to select the affinity for target vapours. They are thermally stable, offer efficient vapour trapping on a MEMS scale platform, provide efficient release of vapour on direct heating and do not interfere with TNT or DNT detection using a GC-MS system. These factors combined with their easy solution processing make them highly suitable for preconcentrator use.

The invention claimed is:

1. An isopotential heater suitable for use in a preconcentrator, wherein said heater comprises at least two electrically conducting paths, wherein the electrical resistances of the at least two electrically conducting paths are substantially equal, such that in use, a uniform heat distribution is achieved, and wherein the heater is a lattice arrangement, to allow an inlet gas to flow through said lattice, wherein the conducting paths are provided by electrically conductive bars and are intersected by electrically conductive crossbars, and wherein the isopotential configuration is provided by a circular lattice arrangement, wherein the conductive bars are in the form of arcs and are intersected by one or more crossbars in the form of struts to form through holes.

2. A heater according to claim 1, wherein the conducting paths are electrically connected to and extend between at least two electrical contact areas.

3. A heater according to claim 1, wherein the electrically conductive crossbars intersect at points of isopotential on said conductive bars.

4. A heater according to claim 1, wherein the cross sectional area of each conductive bar is selected such that they each have substantially the same electrical resistance between the at least two electrical contact areas.

5. A heater according to claim 2, wherein an electrical potential barrier is located between the conductive bars and at least one of the electrical contact areas, to increase the electrical power dissipation in the region of the contact area.

6. A heater according to claim 1, wherein the through hole has a radius which is less than or equal to the diffusion distance of the analyte.

7. A heater according to claim 1, wherein the heater is mounted on an electrically insulating support.

8. A heater according to claim 1, wherein the heater is made from a metalloid or metal.

9. A heater according to claim 8 claims wherein the heater is made from a conductive substrate material, which is capable of being micromachined by deep reactive ion etching.

10. A heater according to claim 8 wherein the heater is prepared from silicon, germanium, nickel, chromium, iron, copper, silver, platinum, palladium or their alloys.

11. A heater according to claim 10 wherein the silicon or germanium is doped with impurities.

12. A heater according to claim 11 wherein the heater is prepared from silicon.

13. A heater according to claim 1, wherein the heater has a diameter of less than 25 mm.

14. A heater according to claim 13 wherein the heater has a diameter of less than 7 mm.

15. A heater according to claim 14, wherein the heater is less than 1 mm thick.

16. A heater according to claim 15 wherein the heater has a thickness in the range of 100 to 500 microns.

17. A heater according to claim 1, wherein the heater has a surface area which is at least 20 $mm^2$.

18. A heater according to claim 17 wherein the surface area of the heater is at least 100 $mm^2$.

19. A heater according to claim 1 wherein the heater has an upper-most surface which is positioned perpendicular to the direction of said inlet gas flow.

20. A heater according to claim 1 wherein the heater has exterior surfaces which are coated with a trapping medium.

21. A heater according to claim 20 wherein the trapping medium is a polymer of intrinsic microporosity.

22. A preconcentrator device comprising a sampling platform for reversibly adsorbing an organic analyte and a heater according to claim 1.

23. A device according to claim 22 which is suitable for use in a hand-held or portable detection system.

24. A chemical detection system for detecting a low concentration of organic analyte comprising, a means for sampling an inlet gas which comprises the organic analyte to be detected, a preconcentrator device according to claim 22, and a detector suitable for detecting said organic analyte.

25. A method of preconcentrating an organic analyte comprising the steps of i) placing a preconcentrator device according to claim 22 in the path of an inlet gas flow to allow adsorption of the target analyte to occur ii) causing an increase in temperature of the heater to desorb said analyte.

26. A method of detecting an organic analyte comprising the steps of preconcentrating an analyte according to claim 25, and passing said desorbed analyte into a detector.

27. A method according to claim 26 wherein the organic analytes are aromatic compounds or compounds which possess a molecular electric quadrupole moment.

28. A method according to claim 27 wherein the compounds are nitrotoluene, dinitrotoluene or trinitrotoluene.

29. A heater according to claim 4, wherein the cross sectional area of each crossbar is selected such that they each have substantially the same electrical resistance between the at least two electrical contact areas.

30. A heater according to claim 12 wherein the heater is part anodised.

31. A preconcentrator device according to claim 22, wherein a trapping medium is applied to the surface of the heater.

* * * * *